United States Patent [19]

Kitamura et al.

[11] Patent Number: 4,723,036
[45] Date of Patent: Feb. 2, 1988

[54] PROCESS FOR PRODUCING PROPYLENE GLYCOL MONOACETATE

[75] Inventors: Takanori Kitamura; Masuhiko Tamura, both of Kurashiki, Japan

[73] Assignee: Kuraray Company, Ltd., Kurashiki, Japan

[21] Appl. No.: 430,694

[22] Filed: Sep. 30, 1982

[30] Foreign Application Priority Data

Oct. 23, 1981 [JP] Japan .................... 56-170281
Jan. 8, 1982 [JP] Japan ..................... 57-2085

[51] Int. Cl.$^4$ ........................................... C07C 67/44
[52] U.S. Cl. ................................... 560/238; 568/454
[58] Field of Search ............... 560/238, 266, 248, 263; 568/454

[56] References Cited

U.S. PATENT DOCUMENTS

| | | | |
|---|---|---|---|
| 3,896,047 | 7/1975 | Aycock et al. | 568/454 |
| 3,904,547 | 9/1975 | Aycock et al. | |
| 4,016,201 | 4/1977 | Rasp et al. | 560/238 |
| 4,052,461 | 10/1977 | Tinker et al. | 568/454 |
| 4,064,145 | 12/1977 | Taylor | 568/454 |
| 4,072,709 | 2/1978 | Tinker | 560/266 |
| 4,258,215 | 3/1981 | Dawes | 568/454 |

OTHER PUBLICATIONS

"Hydroformylation of Unsaturated Compounds with a Cobalt Carbonyl Catalyst", Adkins et al., *J. Am. Chem. Soc.*, 71, 3051–3055.

"Organic Solvents", edited by Weissberger, *Techniques of Chemistry*, vol. II, 3rd edition (1970), pp. 63–65, 236–238, 277–280 and 284.

*Primary Examiner*—Werren B. Lone
*Attorney, Agent, or Firm*—Oblon, Fisher, Spivak, McClelland & Maier

[57] ABSTRACT

There is provided a process for producing propylene glycol monoacetate which comprises the steps of (I) hydroformylating vinyl acetate with a gaseous mixture of hydrogen and carbon monoxide in an organic solvent in the presence of a substantially water-insoluble rhodium complex and a tri-substituted phosphine to form α-acetoxypropionaldehyde, (II) subjecting at least part of the reaction mixture obtained in step (I) to extraction with an aqueous medium to obtain an aqueous layer containing α-acetoxypropionaldehyde and an extraction residue containing the catalyst components, and recycling the extraction residue to the hydroformylation step (I), (III) contacting the aqueous layer containing α-acetoxypropionaldehyde obtained in step (II) with a carboxylic acid ester of general formula (A)

$$C_lH_{2l+1}COOC_mH_{2m+1} \qquad (A)$$

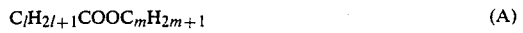

wherein l is an integer of 0 to 4; m is an integer of 1 to 5; and the sum of l and m is 3 to 5, or a dicarboxylic acid ester of general formula (B)

$$ROOC(CH_2)_nCOOR' \qquad (B)$$

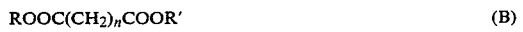

wherein R and R' each is an alkyl group of 2 to 3 carbon atoms; and n is an integer of 0 to 2 to thereby separate α-acetoxypropionaldehyde extractively from the aqueous layer, and (IV) hydrogenating the α-acetoxypropionaldehyde contained in the extract layer as obtained in step (III) in liquid phase in the presence of a Raney nickel or modified Raney nickel catalyst under conditions such that the concentration of α-acetoxypropionaldehyde in the reaction mixture does not exceed 0.1 mole per liter.

Further provided is an improved process for hydrogenating α-acetoxypropionaldehyde which is advantageously employable in the above step (IV).

14 Claims, No Drawings

PROCESS FOR PRODUCING PROPYLENE GLYCOL MONOACETATE

BACKGROUND OF THE INVENTION

1. Field of the Invention

This invention relates to a process for producing propylene glycol monoacetate. More particularly, this invention relates to a process for producing propylene glycol monoacetate which comprises hydroformylating vinyl acetate to α-acetoxypropionaldehyde and, then, hydrogenating the α-acetoxypropionaldehyde to propylene glycol monoacetate, and to a process for producing propylene glycol monoacetate which comprises hydrogenating α-acetoxypropionaldehyde under a defined set of conditions.

1. Description of the Prior Art

While propylene glycol monoacetate is a compound useful as a starting material for the production of propylene glycol and propylene oxide, no commercial process has yet been established for its production. Proposed thus far is a process for producing an acetic acid ester of propylene glycol by oxidation of propylene in acetic acid in the presence of a palladium catalyst (cf. British Pat. No. 1,124,862). In this process, the product compound is separated from the reaction mixture by distillation. During the distillation, however, a part of the palladium catalyst thermally degrades in the distillation vessel so that the catalytic activity cannot easily be maintained at a stable level satisfactory period of time.

There has also been proposed a process in which a compound containing 2 carbon atoms such as ethylene or acetylene is used to prepare propylene glycol monoacetate as an intermediate product which is then converted to an oxygen-containing compound of 3 carbon atoms having the formula $C_3H_6O$ (German Offenlegungsschrift No. 2504981). More particularly, this German Offenlegungsschrift No. 2504981 teaches a process which comprises synthesizing vinyl acetate from ethylene or acetylene, hydroformylating the vinyl acetate with a gaseous mixture of hydrogen and carbon monoxide in the presence of a rhodium catalyst to give α-acetoxypropionaldehyde and hydrogenating this α-acetoxypropionaldehyde in the presence of a metal of Group 8 of Periodic Table of the Elements to provide propylene glycol monoacetate. However, the above conventional process for synthesizing propylene glycol monoacetate has the following disadvantages.

(1) In the hydroformylation of vinyl acetate, separation of the rhodium catalyst from the reaction mixture at the end of the reaction is effected by treating the reaction mixture with hydrogen at high temperature and pressure to thereby precipitate the rhodium catalyst as rhodium metal and recovering the same. However, this recovery of rhodium metal involves a complicated procedure and the accompanying loss of the rhodium catalyst represents an expense which is too great to be disregarded. Moreover, to regenerate the recovered rhodium metal, it must be treated at high temperature and pressure and the treatment requires costly equipment.

(2) When the reaction mixture resulting from the hydroformylation reaction is treated with hydrogen at high temperature and pressure, α-acetoxypropionaldehyde undergoes such undesired side reactions as decarboxylation, polycondensation, isomerization, oxidation, etc.

SUMMARY OF THE INVENTION

Accordingly, an object of this invention is to provide an improved process for producing propylene glycol monoacetate from vinyl acetate via α-acetoxypropionaldehyde.

Another object of this invention is to provide an improved process for producing propylene glycol monoacetate which includes a step of hydrogenating α-acetoxypropionaldehyde with a prolonged catalyst life.

Other objects of this invention will become apparent as the following description proceeds.

DETAILED DESCRIPTION OF THE INVENTION

In accordance with this invention, propylene glycol monoacetate can be produced in high yield by a process which comprises (I) hydroformylating vinyl acetate with a gaseous mixture of hydrogen and carbon monoxide in an organic solvent in the presence of a substantially water-insoluble rhodium complex and a tri-substituted phosphine to form α-acetoxypropionaldehyde, (II) subjecting at least a portion of the reaction mixture obtained in step (I) to extraction with an aqueous medium to obtain an aqueous layer containing α-acetoxypropionaldehyde and an extraction residue containing the catalyst components, and recycling the extraction residue to the hydroformylation step (I), (III) contacting the aqueous layer containing α-acetoxypropionaldehyde obtained in step (II) with a carboxylic acid ester of general formula (A)

$$C_lH_{2l+1}COOC_mH_{2m+1} \qquad (A)$$

wherein l is an integer of 0 to 4; m is an integer of 1 to 5; and the sum of l and m is 3 to 5, or a dicarboxylic acid ester of general formula (B)

$$ROOC(CH_2)_nCOOR' \qquad (B)$$

wherein R and R' each is an alkyl group of 2 to 3 carbon atoms; and n is an integer of 0 to 2 to thereby separate α-acetoxypropionaldehyde extractively from the aqueous layer, and (IV) hydrogenating the α-acetoxypropionaldehyde contained in the extract layer as obtained in step (III) in liquid phase in the presence of a Raney nickel or modified Raney nickel catalyst under conditions such that the concentration of α-acetoxypropionaldehyde in the reaction mixture does not exceed 0.1 mole per liter.

According to the process of the present invention, the catalytic activity of the rhodium complex can be kept stable over a prolonged period of time, since the separation of α-acetoxypropionaldehyde and the rhodium complex from the reaction mixture obtained from the hydroformylation of vinyl acetate is accomplished by extraction with an aqueous medium. In addition, the process of the present invention has the following advantages: (i) excellent operational stability, and (ii) ready availability of main raw materials, i.e., vinyl acetate, carbon monoxide and hydrogen in quantities and at low costs.

The rhodium complex used in the hydroformylation of vinyl acetate may be any desired rhodium complex that is capable of catalyzing the hydroformylation reaction under the reaction conditions used and is substantially insoluble in aqueous media. A number of rhodium complexes which meet these qualifications are known, and generally these known rhodium complexes can be employed for the purposes of the present invention. Suitable rhodium complexes include $HRh(CO)(PA_3)_3$, wherein A is an aryl group, $RhCl(PA_3)_3$, $Rh(acac)_3$, wherein acac is an acetylacetonyl group, $Rh(OAc)_3$, wherein OAc is an acetoxy group, $Rh_4(CO)_{12}$, $Rh_6(CO)_{16}$, $[Rh(CO)_2(PA_3)_2]_2$, $RhCl_3 \cdot 3H_2O$, $Rh_2O_3$, and the like. Among these compounds, rhodium compounds of the formula $HRh(CO)(PA_3)_3$ are especially desirable from the viewpoint of such considerations as catalytic activity, solubility, ease of handling, and the like. The rhodium complex is generally used in a concentration of 0.1 to 10 mmoles per liter of the hydroformylation reaction mixture. The organic solvent used for the practice of the present invention should be a substantially water-insoluble solvent in order to facilitate the subsequent extraction of the reaction mixture with an aqueous medium. Many organic solvents qualify in this regard, but when such physical and chemical properties are considered as the solubility of the catalyst components, the loss of the catalyst components due to dissolution into the aqueous layer, price, and possible influences on the subsequent separation step, it is advantageous to employ an aromatic hydrocarbon which may optionally be substituted by lower alkyl groups. For example, preferred solvents include benzene, toluene, xylene, ethylbenzene, and the like and substituted or unsubstituted, saturated alicyclic hydrocarbons such as cyclohexane, methylcyclohexane, and the like. The aforementioned tri-substituted phosphine compound is represented by the general formula $PR'R''R'''$, wherein $R'$ and $R''$ are each an aromatic hydrocarbon group and, $R'''$ is an aromatic hydrocarbon group or a saturated aliphatic hydrocarbon group of at least 3 carbon atoms. Examples of such tri-substituted phosphine are substituted or unsubstituted triarylphosphines, e.g., triphenylphosphine, tritolylphosphine, trinaphthylphosphine, and the like and diarylalkylphosphines such as diphenylpropylphosphine, diphenylhexylphosphine, and the like. Particularly preferred are substituted or unsubstituted triarylphosphines. The proper amount of such a tri-substituted phosphine is within the range of about 5 to about 50 moles per gram atom of rhodium and, more specifically, it is advantageous to employ the tri-substituted phosphine in a concentration of 10 to 150 millimoles per liter of the hydroformylation reaction mixture.

In the practice of the present invention, the hydroformylation of vinyl acetate is generally conducted at a temperature of 50° to 120° C., a carbon monoxide partial pressure of 4 to 70 kg/cm² (absolute), a reaction pressure of 25 to 150 kg/cm² and a molar hydrogen-to-carbon monoxide ratio of 0.5 to 5. The hydroformylation reaction can be carried out continuously or batchwise in a reaction vessel equipped with a stirrer or in a reactor of the bubble tower type, which is known per se. In order to suppress a build-up of reaction heat, to improve the selectivity for α-acetoxypropionaldehyde, and to prevent accumulation of high-boiling by-products, it is advantageous to feed vinyl acetate continuously into the reactor in such a manner that the concentration of vinyl acetate in the reaction system will be within a certain range (for example, 0.25 to 1.5 moles/liter). The concentration of α-acetoxypropionaldehyde in the reaction mixture is preferably maintained in the range of about 0.5 to 3 moles per liter of the reaction mixture in view of such factors as the accumulation of high-boiling by-products, the losses of the rhodium complex and tri-substituted phosphine resulting from dissolution of the materials into the aqueous layer, the efficiency of extraction of α-acetoxypropionaldehyde into the aqueous medium and so on.

The reaction mixture containing α-acetoxypropionaldehyde, which is obtained by the hydroformylation of vinyl acetate [step (I)] is subjected to extraction with an aqueous medium in step (II), whereby α-acetoxypropionaldehyde is dissolved into the aqueous phase. Suitable aqueous extraction media include water and aqueous solutions containing a small proportion (for example, about 5 to 10%) of acetic acid. Suitable extraction equipment includes any of the known extraction apparatus of the stirring vessel type, the RDC (rotary disk contractor) type, and perforated plate towers. However, an RDC type extraction apparatus is most desirable from the point of view of the efficiency of extraction of α-acetoxypropionaldehyde, losses of the rhodium complex and tri-substituted phosphine because of dissolution into the aqueous layer, and the like. A detailed investigation by the present inventors has shown that the degree of extraction of α-acetoxypropionaldehyde into the aqueous layer and losses of the rhodium complex and tri-substituted phosphine resulting from dissolution in the aqueous layer are dependent on such factors as efficiency of contact between the aqueous medium and hydroformylation reaction mixture, extraction temperature, concentration α-acetoxypropionaldehyde in the reaction mixture, ratio by volume of the aqueous medium to the reaction mixture and the atmosphere at the time of extraction. Thus, a higher efficiency of contact between the aqueous medium and the hydroformylation reaction mixture, lower extraction temperatures and higher ratio by volume of the aqueous medium to the hydroformylation reaction mixture tend to promote the extent of extraction of α-acetoxypropionaldehyde into aqueous medium and reduce losses of the rhodium complex and trisubstituted phosphine resulting from dissolution of the materials into the aqueous layer. The extraction temperature is selected from the range from about 5° to 40° C. The volume ratio of the aqueous medium to the hydroformylation reaction mixture depends on the concentration of α-acetoxypropionaldehyde in the reaction mixture. However, the ratio should preferably be selected within the range of 0.3–3 when said concentration is about 0.5 to 3 moles per liter of the reaction mixture. The extraction with an aqueous medium in step (II) is preferably conducted under an atmosphere of a substantially oxygen-free inert gas such as nitrogen, helium or argon, a gaseous mixture of hydrogen and carbon monoxide, or a gaseous mixture of hydrogen and carbon monoxide diluted with one of the above-mentioned inert gases. In this manner, loss of the rhodium complex resulting from dissolution of materials into the aqueous layer can be minimized. While the extraction may be conducted in a batchwise fashion, a continuous process is preferred for commercial production purposes.

The extraction residue obtained in step (II), which contains the catalyst components, is recycled to the hydroformylation step (I) for reuse. In this instance, a part of the extraction residue, after being subjected to a known catalyst activation treatment, if necessary, is recycled to the hydroformylation step.

The aqueous layer containing α-acetoxypropionaldehyde as obtained in step (II) is now contacted with a carboxylic acid ester of general formula (A) or a dicarboxylic acid ester of general formula (B) to extract the α-acetoxypropionaldehyde from said aqueous layer [step (III)]. In this step (III), the extraction temperature is preferably about 5° C. to about 90° C., more preferably about 20° C. to about 80° C. Whereas the degree of extraction of α-acetoxypropionaldehyde tends to rise with increase in temperature, temperatures exceeding 90° C. are undesirable because portions of the α-acetoxypropionaldehyde and the extracting solvent are hydrolyzed during the extraction procedure. The extraction may be carried out either continuously or batchwise. However, continuous extraction is industrially more advantageous.

Any extraction apparatus can be used such as a known stirring or perforated plate extraction tower. The carboxylic acid ester of formula (A), which is used as the extracting solvent, includes, among others, n-butyl formate, n-amyl formate, ethyl acetate, n-propyl acetate, isopropyl acetate, tert-butyl acetate, methyl propionate, ethyl propionate, methyl butyrate, methyl isobutyrate, and methyl valerate. Among these carboxylic acid esters, isopropyl acetate, n-propyl acetate and ethyl propionate are especially preferred from the viewpoint of the extractability of α-acetoxypropionaldehyde, the hydrolyzability, solubility in water and boiling point of the carboxylic acid ester, the composition of the azeotrope with water, the azeotropic point, and the solubility of water in the carboxylic acid ester, among others. When the carboxylic acid esters in which the sum of l and m in formula (A) is 2 or less, such as methyl acetate and ethyl formate, are used as the extracting solvents, α-acetoxypropionaldehyde can easily be extracted into the solvents. However, at the same time, water is readily extracted into the solvent layer, so that efficient extraction of α-acetoxypropionaldehyde cannot be achieved. The use of those carboxylic acid esters in which the sum of l and m in formula (A) is 6 or more such as n-butyl caprate as the extracting solvent, is disadvantageous from the industrial standpoint because α-acetoxypropionaldehyde is barely extracted with the solvents.

Suitable examples of the dicarboxylic acid ester of general formula (B) include diethyl oxalate, diisopropyl oxalate, ethyl isopropyl oxalate, diethyl malonate and diethyl succinate. Among these dicarboxylic acid ester, diethyl oxalate, diethyl malonate and diethyl succinate are especially preferred from the viewpoint of extractability of α-acetoxypropionaldehyde, the hydrolyzability, solubility in water and boiling points of the dicarboxylic acid esters, the solubility of water in the dicarboxylic acid esters, other physical properties, the generality of use and the prices of the solvents, among others. When those dicarboxylic acid esters of formula (B), wherein n is an integer of 0 to 2 and each of R and R' is methyl, such as dimethyl succinate, are used as the extracting solvent, α-acetoxypropionaldehyde can easily be extracted into the solvents but at the same time water is readily soluble in the solvents, so that efficient extractive separation of α-acetoxypropionaldehyde cannot be attained. The use of those dicarboxylic acid esters of formula (B), wherein n is an integer of 3 or more, such as dimethyl adipate, is disadvantageous from the industrial standpoint because α-acetoxypropionaldehyde is barely extracted with such solvents, and/or the boiling points thereof are too high. When those dicarboxylic acid esters of formula (B), wherein n is an integer of 3 or more and R and R' are each an alkyl group containing 2 or 3 carbon atoms are used as the extracting solvent, a prolonged period of time is required for phase separation because the specific gravities of the solvent are very close to the specific gravity of water. For most practical purposes from about 0.5 to about 5 volumes of the carboxylic acid ester of formula (A) or the dicarboxylic acid ester of formula (B) are used per volume of the aqueous solution containing α-acetoxypropionaldehyde. The extraction residue can be recycled to step (II) as it is for reuse as the aqueous medium.

The α-acetoxypropionaldehyde in the extract layer obtained in step (III) is hydrogenated in step (IV). The catalyst used for this hydrogenation of α-acetoxypropionaldehyde is Raney nickel or Raney nickel as modified with at least one of such metals as chromium, rhenium, molybdenum, tungsten, titanium, iron, lead, manganese, etc. While the hydrogenation cayalysts commonly employed include not only the above catalysts but also stabilized nickel catalysts represented by nickel-diatomaceous earth rhutenium-carbon, etc., it has been found that for the hydrogenatin of α-acetoxypropionaldehyde, Raney nickel and modified Raney nickel catalysts are advantageous in terms of catalytic activity. Any of the Raney nickel and modified Raney nickel catalysts is used in a concentration of 1.0 to 10 weight percent, preferably 0.5 to 5 weight percent, relative to the reaction mixture just as in the case of hydrogenation reactions in general. The hydgrogenation of α-acetoxypropionaldehyde according to this invention must be conducted under conditions such that the concentration of α-acetoxypropionaldehyde in the reaction mixture will not exceed 1.0 mole per liter. Under these conditions, the catalyst activity can be maintained stably for a long time. If the concentration of α-acetoxypropionaldehyde in the reaction mixture exceeds 0.1 mole/liter, the catalyst life tends to become shortened probably due to side reactions such as the polymerization of α-acetoxypropionaldehyde. The concentration of α-acetoxypropionaldehyde in the reaction mixture can be easily controlled by adding the extract layer containing α-acetoxypropionaldehyde either continuously or intermittently to the reaction system. To maintain the concentration of α-acetoxypropionaldehyde within the above limits, it is also an effective procedure to maintain the concentration of the Raney nickel or modified Randel nickel catalyst in the reaction mixtures at a comparatively high level so as to increase the rate of comsumption of α-acetoxypropionaldehyde by reaction.

In conducting the hydrogenation reaction of α-acetoxypropionaldehyde, it has been found that the catalyst life can be further improved by conducting the reaction in the presence of 0.01 to 10 weight percent, based on the reaction mixture, of water and under the above-mentioned conditions such that the concentration of α-acetoxypropionaldehyde in the reaction mixture does not exceed 0.1 mole/liter. If the amount of water is less than 0.01 weight percent based on the reaction mixture, the stabilizing effect of water on the catalyst will be substantially be realized, whereas the presence of water in an amount exceeding 10 weight percent will cause a substantially hydrolysis of α-acetoxypropionaldehyde and the catalyst life will rather tend to decrease. The preferred amount of water is 0.1 to 10 weight percent relative to the reaction mixture.

This hydrogenation reaction is conducted at a hydrogen partial pressure of 1 to 150 and preferably 5 to 100 absolute atmospheres. The reaction temperature is selected from within the range of 70° to 180° C. and preferably of 90° to 160° C. The reaction can be conducted in whichever of a stirring type reaction vessel and a bubble tower reactor, both of which are known per se. While the reaction may be conducted batchwise or continuously, a continuous process is commercially advantageous. In order to increase the conversion of α-acetoxypropionaldehyde, it is also preferable to provide a finishing hydrogenation vessel.

Propylene glycol monoacetate can be isolated from the hydrogenation reaction mixture by removing the Raney nickel or modified Raney nickel for example by filtration, precipitation, centrifugation or the like and subjecting the filtrate or supernatant to the conventional distillation procedure. When it is desired to finally provide propylene glycol by hydrolizing propylene glycol monoacetate, the propylene glycol monoacetate can be extracted into an aqueous layer by removing the nickel catalyst from the reaction mixture and extracting the filtrate with water.

Having generally described this invention, a further understanding can be obtained by reference to certain specific examples which are provided herein for purpose of illustration only and are not intended to be limiting unless otherwise specified.

EXAMPLE 1

(i) Synthesis of α-acetoxypropionaldehyde and separation of the same from the reaction mixture The synthesis of α-acetoxypropionaldehyde and extraction of this material with water were conducted in the apparatus described below. The whole procedure was performed under conditions which excluded the entry of air into the system as much as possible and distilled water and toluene were used after displacement and removal of dissolved oxygen with nitrogen gas.

Reactor: A one-liter stainless steel autoclave equipped with thermometer, stirrer, liquid feed pump, liquid sampling outlet, gas inlet and gas outlet was used.

Extractor: A one-liter four-necked flask equipped with thermometer, stirrer, liquid feed inlet, liquid sampling outlet, gas inlet and gas outlet was used as the extractor. The extractor was connected to the above-mentioned autoclave by a pipe.

A solution of 918 mg (1.0 millimole) of $HRh(CO)[P(C_6H_5)_3]_3$ and 2,620 mg (10 millimoles) of triphenylphosphine in 420 ml of toluene was washed with two 420-ml portions of distilled water at room temperature in an atmosphere of a mixed gas composed of hydrogen and carbon monoxide ($H_2/CO$ mole ratio 2/1) and charged into the above-mentioned autoclave. The atmosphere within the autoclave was replaced with a hydrogencarbon monoxide mixture ($H_2/CO$ mole ratio 2/1). The autoclave was then pressurized to 30 kg/cm² (gauge) with the same gas mixture as above and heated in an oil bath so that the inside temperature was maintained constantly at 70° C. Stirring was started at the rate of 600 rpm (revolution per minute), and 71 g (830 millimoles) of vinyl acetate was introduced continuously over 1.5 hours. The off-gas flow rate was adjusted to 20 liters per hour. In this manner, the reaction was conducted at 70° C. and 30 kg/cm² (gauge) with stirring. Low boiling compounds (vinyl acetate, propionaldehyde, toluene, etc.) present in the off-gas were collected in a trap placed in a dry ice-acetone bath. After completion of the feeding of vinyl acetate starting material, stirring was continued under the same conditions for 2 hours so as to allow the reaction to proceed further. Analysis of the reaction mixture by gas chromatography revealed that the conversion of vinyl acetate in 3.5 hours amounted to 90% and the selectivity toward α-acetoxypropionaldehyde was 93% based on the converted vinyl acetate. The reaction mixture was cooled to room temperature and then transferred by taking advantage of the internal pressure of the reactor to the above-mentioned extractor in which the atmosphere had been replaced with a hydrogen-carbon monoxide mixture ($H_2/CO$ mole ratio 2/1). The extractor was further charged with 90 ml of nitrogen-purged distilled water, and the extraction of α-acetoxypropionaldehyde from the toluene solution (reaction mixture) with water was effected by stirring the solution at the rate of 500 rpm at 20° C. for 20 minutes. The aqueous layer which formed upon standing was removed from the system, and 90 ml of distilled water was added to the remaining toluene solution and the extraction was again conducted under the same conditions (total water/reaction mixture volume ratio = ½). These two extraction procedures transferred 92% of the α-acetoxypropionaldehyde to the aqueous layer. The concentration of rhodium in the aqueous layer (as determined by atomic absorption spectrometry) was 0.05 ppm and that of phosphorus compound (as determined by colorimetry) was 10 ppm as phosphorus. The extraction residue, namely the toluene solution containing the catalyst components, was transferred to the above-mentioned autoclave by taking advantage of the pressure of the hydrogen-carbon monoxide mixture. Vinyl acetate was added continuously at the rate of 48 g/hr for 80 minutes with stirring under the conditions of 70° C., 30 kg/cm² (gauge) and 600 rpm. Thereafter, the reaction was allowed to proceed further by stirring the solution for 2 hours. Then, the reaction mixture was subjected to extraction with water by following the same procedure under the same conditions described above. The extraction residue was again fed under pressure to the autoclave and the hydroformylation of vinyl acetate was conducted. In this manner, the hydroformylation of vinyl acetate followed by extraction with water was repeated 10 times in all. As a result, about 2.3 liters total of the aqueous extract layer was obtained. The conversions of vinyl acetate in the 3rd, 6th and 10th runs were 91%, 90% and 91%, respectively, and the concentrations of rhodium in the aqueous extract layer were 0.05 ppm, 0.06 ppm and 0.06 ppm (as rhodium), respectively. These conversion and concentration values did not show any substantial change throughout the repeated runs. The aqueous extract layer in each run was stored at 5° C. under a nitrogen atmosphere.

(ii) Separation of α-acetoxypropionaldehyde from the aqueous extract layer

The atmosphere in a 1-liter glass extractor fitted with a stirrer, reflux condenser and thermometer was replaced with nitrogen gas, and under a nitrogen gas atmosphere, the extractor was charged with 240 ml of the above aqueous extract layer and 480 ml of $N_2$-purged isopropyl acetate. The mixture was stirred at 60° C. and 500 rpm for 30 minutes to extract the α-acetoxypropionaldehyde. By this extraction procedure, 78% of α-acetoxypropionaldehyde in aqueous solution was extracted into an isopropyl acetate layer. This isopropyl acetate layer contained about 4.3 weight percent of water. The above extraction procedure was repeated for a total of 5 times to give about 2.5 l of an isopropyl acetate solution of α-acetoxypropionaldehyde.

(iii) Hydrogenation of α-acetoxypropionaldehyde

A stainless steel autoclave of electromagnetic stirring type, having a capacity of 500 ml and equipped with a thermometer, pressure regulator and off-gas flow control valve and starting material feed inlet was charged with 0.68 g of a Raney nickel catalyst (Kawaken Fine Chemicals, Ltd.)(0.68 g as nickel metal) previously washed with water, ethanol and isopropyl acetate in that order and 50 ml of isopropyl acetate solvent and after the internal atmosphere was sufficiently replaced with hydrogen gas, hydrogen gas was introduced to 20 kg/cm² (absolute pressure). Thereafter, the autoclave was heated in an oil bath so that the inside temperature was maintained constantly at 100° C. Stirring was commenced at 600 rpm and the isopropyl acetate solution of α-acetoxypropionaldehyde obtained in (ii) above was continuously fed at a rate of 60 ml/hr. for 3 hours. During feeding of the starting material, the internal pressure was maintained at a constant level of 20 kg/cm² by means of the pressure regulator and the flow rate of off-gas was controlled at 15 l/hr. with the off-gas flow control valve. After feeding of the starting material, the stirring was further continued at the same temperature and pressure for 15 minutes, whereby the reaction was carried to completion. The concentration of α-acetoxypropionaldehyde in the reaction mixture at completion of feeding of the starting material was 0.005 mole/l. Gas chromatographic analysis of the reaction mixture showed that the hydrogenation rate of α-acetoxypropionaldehyde was 100 percent and the selectivity for propylene glycol monoacetate was 99.5% (based on converted α-acetoxypropionaldehyde). The reaction mixture was filtered to remove the catalyst and the filtrate was distilled at atmospheric pressure to remove an azeotropic mixture of isopropyl acetate and water and isopropyl acetate and, then, at reduced pressure, to remove a small amount of acetic acid. Then, about 17 g of propylene glycol monoacetate was obtained as a distillate at 95° C./20 mmHg.

EXAMPLES 2 to 7

The same hydroformylation reaction of vinyl acetate and the same aqueous extraction procedure as described in Example 1 were repeated for a total of 10 times except that 100 ml of distilled water was used per extraction to give about 2.5 l of an aqueous solution containing about 2.5 moles/l of α-acetoxypropionaldehyde and small amounts of acetic acid and propionaldehyde. Then, the same extractive separation and hydrogenation of α-acetoxypropionaldehyde as those described in Example 1 (ii) and (iii) were repeated except that various monocarboxylic and dicarboxylic acid esters were used in lieu of isopropyl acetate and various modified Raney nickel catalysts in lieu of Raney nickel. The results are summarized in Table 1.

TABLE 1

| Example | Extraction solvent | Extraction temperature (°C.) | Extraction rate of APA$^{(1)}$ (%) | Hydrogenation catalyst | Reaction temperature (°C.) | Reaction pressure (kg/cm²) | Concentration of water in APA charged (wt. %) | Concentration of APA in reaction mixture$^{(4)}$ (mole/l) | Selectivity for PGMA$^{(5)}$ (%) |
|---|---|---|---|---|---|---|---|---|---|
| 2 | Ethyl propionate | 70 | 78 | Raney nickel | 100 | 10 | 4.5 | 0.015 | 99.5 |
| 3 | n-Butyl formate | 60 | 76 | Rhenium-modified Raney nickel$^{(2)}$ | 100 | 20 | 4.1 | 0.030 | 99 |
| 4 | n-Propyl acetate | 60 | 77 | Molybdenum-modified Raney nickel$^{(3)}$ | 100 | 15 | 4.3 | 0.025 | 99.5 |
| 5 | Diethyl succinate | 60 | 84 | Raney nickel | 120 | 10 | 3.8 | 0.010 | 99 |
| 6 | Diethyl malonate | 60 | 82 | Molybdenum-modified Raney nickel$^{(3)}$ | 120 | 15 | 3.5 | 0.015 | 99 |
| 7 | Deithyl oxalate | 60 | 80 | Molybdenum-modified Raney nickel$^{(3)}$ | 140 | 20 | 3.4 | 0.008 | 99 |

$^{(1)}$APA stands for α-acetoxypropionaldehyde.
$^{(2)}$Powders of an Ni—Re—Al alloy consisting of 47.5 wt. % Ni, 2.5 wt. % Re and 50 wt. % Al were developed and washed with water, ethanol and the corresponding extraction solvent.
$^{(3)}$Powders of a Ni—Mo—Al alloy consisting of 47.0 wt. % Ni, 3.0 wt. % Mo and 50 wt. % Al were developed and washed with water, ethanol and the corresponding extraction solvent.
$^{(4)}$The residual concentration of APA at completion of addition of APA. The reaction solvent was the same as the extraction solvent.
$^{(5)}$PGMA stands for propylene glycol monoacetate. The selectivity values are based on converted APA.

EXAMPLE 8

The steps (i) and (ii) of Example 1 were respectively repeated for a total of 40 times to give about 20 l of an isopropyl acetate layer containing about 0.9 mole/l of α-acetoxypropionaldehyde. A distillation apparatus previously purged with nitrogen gas was charged with 2 l of the above isopropyl acetate layer and while the liquid temperature was held at 60° C., about 72 g of the water contained in the isopropyl acetate layer was distilled off as an azeotropic mixture with isopropyl acetate under a reduced pressure of 250 mmHg. Then, isopropyl acetate was added to the residual liquid in the apparatus to prepare 2 l of an isopropyl acetate solution of α-acetoxypropionaldehyde containing about 0.2 weight % of water. The isopropyl acetate solution of α-acetoxypropionaldehyde thus obtained was subjected to hydrogenation under the same conditions as described in Example 1-(iii). After completion of the reaction, the autoclave was allowed to stand, after which 180 ml of a supernatant of the reaction mixture was removed by taking advantage of the internal pressure. After this procedure, the autoclave was charged with the above isopropyl acetate solution of α-acetoxypropionaldehyde and the hydrogenation of α-acetoxypropionaldehyde was repeated under the same conditions and in the same manner as described above. As a result, the rates of hydrogenation of α-acetoxypropionaldehyde in the 4th, 6th and 8th runs were 100%, 99.5% and 99%, respectively.

EXAMPLES 9 TO 10 AND CONTROL EXAMPLES 1 TO 3

In the procedure of Example 8, the amount of water distilled from the isopropyl acetate layer was varied to prepare isopropyl acetate solutions of α-acetoxypropionaldehyde containing various concentrations of water. Otherwise, the hydrogenation reaction was conducted under the same conditions and in the same manner as Example 8. However, in Control Example 2, α-acetoxypropionaldehyde was isolated by distillation from the isopropyl acetate layer and dissolved in ethylene glycol diacetate. The resultant ethylene glycol diacetate solution containing 0.9 mole/l of α-acetoxypropionaldehyde was used. In Control Example 3, the amount of isopropyl acetate to be added to the residual liquid after distillative removal of water from the isopropyl acetate layer was reduced and the resultant concentrated isopropyl acetate solution of α-acetoxypropionaldehyde was charged into the reactor so as to adjust the concentration of α-acetoxypropionaldehyde in the reaction mixture. The results are shown in Table 2.

TABLE 2

| | Concentration of water in reaction mixture (wt. %) | Concentration of APA in reaction mixture (moles/l) | Conversion of APA (%) 1st run | Conversion of APA (%) 6th run |
|---|---|---|---|---|
| Example | | | | |
| 9 | 1.0 | 0.010 | 100 | 99 |
| 10 | 2.5 | 0.015 | 100 | 97 |
| Control Example | | | | |
| 1 | 0.002 | 0.015 | 100 | 90 |
| 2 | 15.0 | 0.07 | 97 | 75[6] |
| 3 | 1.0 | 0.20 | 98 | 69[6] |

[6] The conversion of APA in the 4th run.

What is claimed is:

1. A process for producing propylene glycol monoacetate which comprises
(I) hydroformylating vinyl acetate with a gaseous mixture of hydrogen and carbon monoxide in an organic solvent in the presence of a substantially water-insoluble rhodium complex and a tri-substituted phosphine to form α-acetoxypropionaldehyde,
(II) extracting at least part of the reaction mixture obtained in step (I) with an aqueous medium, thereby obtaining an aqueous layer containing α-acetoxypropionaldehyde and an extraction residue containing the catalyst components, and recycling the extraction residue to the hydroformylation step (I);
(III) contacting the aqueous layer containing a-acetoxypropionaldehyde obtained in step (II) with a carboxylic acid ester of general formula (A)

wherein l is an integer of 0 to 4; m is an integer of 1 to 5; and the sum of l and m is 3 to 5, or a dicarboxylic acid ester of general formula (B)

wherein R and R' each is an alkyl group of 2 to 3 carbon atoms; and n is an integer of 0 to 2 to thereby separate α-acetoxypropionaldehyde extractively from the aqueous layer, and
(IV) hydrogenating the α-acetoxypropionaldehyde contained in the extract layer as obtained in step (III) in liquid phase in the presence of a Raney nickel or modified Raney nickel catalyst under conditions such that the concentration of α-acetoxypropionaldehyde in the reaction mixture does not exceed 0.1 mole per liter.

2. A process according to claim 1 wherein the hydroformylation reaction of vinyl acetate in step (I) is conducted at a reaction temperature of 50° to 120° C.

3. A process according to claim 1 wherein the extraction procedure of the step (II) is conducted at a temperature of about 5° to 40° C.

4. A process according to claim 1 wherein the carboxylic acid ester of general formula (A) which is selected from the group consisting of isopropyl acetate, n-propyl acetate and ethyl propionate, is used.

5. A process according to claim 1 wherein the dicarboxylic acid ester of general formula (B) which is selected from the group consisting of diethyl oxalate, diethyl malonate and diethyl succinate, is used.

6. A process according to claim 1 wherein the hydrogenation reaction of α-acetoxypropionaldehyde in step (IV) is conducted at an absolute hydrogen partial pressure of 1 to 150 atmospheres and a reaction temperature of 70° to 180° C.

7. A process according to claim 6 wherein the reaction conducted in the presence of 0.01 to 10 weight percent, based on the reaction mixture, of water.

8. A process for producing propylene glycol monoacetate which comprises hydrogenating α-acetoxypropionaldehyde in liquid phase in the presence of a Raney nickel or modified Raney nickel catalyst and 0.01 to 10 weight percent, based on the reaction mixture, of water and under conditions such that the concentration of α-acetoxypropionaldehyde in the reaction mixture does not exceed 0.1 mole per liter.

9. A process according to claim 1 wherein the organic solvent of step (I) is a substantially water-insoluble solvent.

10. A process according to claim 9 wherein the substantially water insoluble solvent is an aromatic hydrocarbon which may optionally be substituted with lower alkyl groups.

11. A process according to claim 1 wherein the aqueous medium of step (II) is selected from water and water containing 5 to 10 percent of acetic acid.

12. A process according to claim 1 wherein the extraction procedure of step (II) is conducted such that the volume ratio of the aqueous medium to the hydroformylation reaction mixture is in the range of 0.3–3.

13. A process according to claim 1 wherein the extraction procedure of step (II) is conducted under an atmosphere of a substantially oxygen-free inert gas.

14. A process according to claim 1 wherein the contacting procedure of step (III) is conducted at a temperature of 5° to 90° C.

* * * * *